United States Patent [19]

Trummlitz et al.

[11] Patent Number: 4,626,325

[45] Date of Patent: Dec. 2, 1986

[54] PROCESS FOR THE PREPARATION OF 4-HYDROXY-1,2-BENZISOTHIAZOL-3(2H)-ONE-1,1-DIOXIDE

[75] Inventors: Gunter Trummlitz, Warthausen; Wolfgang Eberlein, Biberach; Wolfhard Engel, Biberach; Gerhard Mihm, Biberach, all of Fed. Rep. of Germany

[73] Assignee: Karl Thomae GmbH, Biberach an der Riss, Fed. Rep. of Germany

[21] Appl. No.: 841,392

[22] Filed: Mar. 19, 1986

[30] Foreign Application Priority Data

Mar. 19, 1985 [DE] Fed. Rep. of Germany ....... 3509819

[51] Int. Cl.$^4$ ............................................... C25C 3/00
[52] U.S. Cl. .................................. 204/59 R; 426/548; 548/210; 548/211
[58] Field of Search ............. 204/59 R; 548/211, 210; 426/548

[56] References Cited

U.S. PATENT DOCUMENTS 4,057,555  11/1977  Kolke et al. ..................... 548/210
4,140,697  2/1979   Batcho et al. .................... 426/548
4,404,230  9/1983   Trummlitz et al. ............... 426/548

*Primary Examiner*—Arthur P. Demers
*Attorney, Agent, or Firm*—David E. Frankhouser; Alan R. Stempel

[57] ABSTRACT

The specification describes a process for preparing 4-hydroxy-1,2-benzisothiazol-3(2H)-one-1,1-dioxide, a sweetener, from 1,2-benzisothiazol-3(2H)-one-1,1-dioxide by anodic oxidation in the presence of trifluoroacetic acid or trifluoromethanesulfonic acid and, optionally, in the presence of salts which increase the conductivity. The oxidation is effected in an anhydrous medium and the 4-trifluoroacetoxy-1,2-benzisothiazol-3(2H)-one-1,1-dioxide formed as an intermediate when, for example, trifluoroacetic acid is used is decomposed with water to obtain the desired end product.

8 Claims, No Drawings

PROCESS FOR THE PREPARATION OF 4-HYDROXY-1,2-BENZISOTHIAZOL-3(2H)-ONE-1,1-DIOXIDE

The invention relates to a new process for preparing 4-hydroxy-1,2-benzisothiazol-3(2H)-one-1,1-dioxide. This compound has the formula

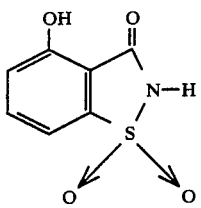

and was described, in European Pat. No. 38458 (corresponding to U.S. Pat. No. 4,404,230) as a sweetener with superior sensory qualities. The same publication described four methods of preparing it but all these methods involved 4 to 7 steps, beginning with low-priced starting materials. However, since sweeteners should be produced in large quantities and as cheaply as possible, it was necessary to find the simplest possible method of synthesis which could be carried out on a large industrial scale starting from an inexpensive starting material which is available in large quantities. This problem has now been solved by means of the present invention which comprises oxidising 1,2-benzisothiazol-3(2H)-one-1,1-dioxide (Saccharin ®(R), see formula II below) anodically in the presence of trifluoroacetic acid or trifluoromethanesulfonic acid in a single-step process to obtain 4-hydroxy-1,2-benzisothiazol-3(2H)-one-1,1-dioxide. The starting compound is mass-produced and is therefore available as a cheap starting compound. The following reaction plan illustrates this oxidation:

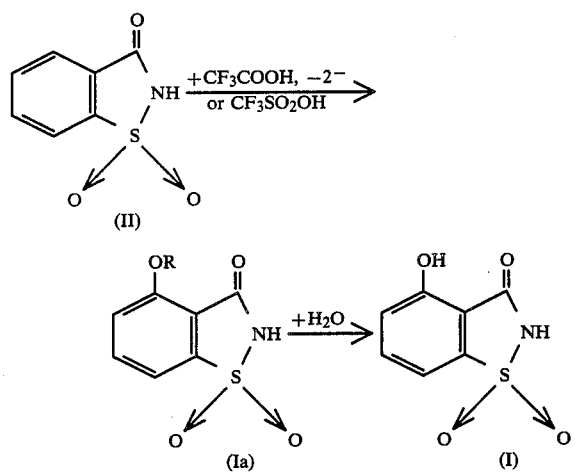

In the compound of formula Ia, R is the $CF_3CO-$ or $CF_3SO_2-$ group.

The reaction, which proceeds with the elimination of water, is effected in the presence of trifluoroacetic acid, in the presence of a conducting salt and optionally an organic solvent at temperatures of between 0° C. and 50° C., but preferably at ambient temperature. The anodic oxidation may be carried out as either a discontinuous or a continuous process.

In the discontinuous process, the product formed is removed by suitable methods, preferably after a certain charge quantity has passed through, and the unreacted compound of formula II is supplemented by the addition of further starting compound and then again oxidised by electrochemical methods. When the process is carried out continuously, the product of formula I formed is continuously isolated from the reaction mixture; the latter is recycled into the anodic oxidation, supplemented by fresh starting material of formula II. The compound of formula Ia formed as an intermediate is decomposed using water, irrespective of the manner in which the process is performed. For the anodic oxidation a large number of organic solvents and electrolytes are suitable, the only common factor being that they have the highest possible anodic decomposition potential. Examples of suitable solvents include dichloromethane, sulfolane, acetonitrile, dimethylformamide, dimethylsulfoxide, dimethylacetamide, tetrahydrofuran, pyridine, acetic acid or nitromethane. However, it is also possible to use mixtures of these solvents. Particularly suitable conducting salts are tetraalkylammonium fluoborates such as tetraethylammonium fluoroborate, tetra-n-butylammonium fluoroborate and also alkali metal trifluoroacetates such as sodium or potassium trifluoroacetate or alkali metal perchlorates such as sodium or lithium perchlorate. The addition of aluminium oxide or trifluoroacetic anhydride has a very favourable effect on the yield in many cases, these substances ensuring anhydrous conditions.

The voltage required depends to a large extent on other reaction conditions, for example the nature and configuration of the electrodes, the electrode gaps, the type of electrolyte and solvent used. The potential can be monitored by the use of a reference electrode. This potential is selected so that there is no formation of decomposition products such as hexafluoroethane when using trifluoroacetic acid and no further oxidation of the intermediate stage of formula Ia.

Generally, a charge flow of from 2 to 4 F per mol of reacted educt is used for the reaction.

The electrodes may be produced from a variety of possible materials, the only prerequisite being that they have a certain stability to oxidation. Thus, a whole range of oxide electrodes are suitable such as lead dioxide and also platinum or other noble metal electrodes and also, under industrial conditions, lead, lead dioxide, glassy carbon, graphite or carbon electrodes. The electrodes may be in plate or wire-gauze form, for example in a form in which the cathode is a spiral located in the centre of a wire gauze cylinder which acts as the anode.

When carrying out electrolytic oxidation it is also possible to separate the cathode space from the anode space by means of a semipermeable diaphragm in order to prevent reduction, in the cathode space, of the compound of formula I formed. It is advisable to use materials which are resistant to solvents and have low resistance.

The reaction can be carried out in the electrolysis apparatus conventionally used, such as those described by L. Eberson and H. Schäfer in "Fortschritte der chemischen Forschung/Topics in Current Chemistry", 21, pages 1 to 39 (Springer-Verlag, Berlin-Heidelberg-New York 1971), whilst it is particularly advantageous to use capillary gap cells.

It is known that in the presence of trifluoroacetic acid and sodium trifluoroacetate and organic solvents such as acetone the anodic oxidation of alkyl-aromatic compounds or acyl-aromatic compounds results in products which are trifluoroacetoxylated at the nucleus and possibly in the side chains. It is assumed that the nuclear substitution proceeds via aromatic radical cations which are particularly stable in the strong trifluoroacetic acid. Various isomers are formed; the isomer distribution discovered corresponds to the positive charge density distribution calculated by the INDO method for the aromatic radical cation (cf Z. Blum, L. Cedheim and K. Nyberg, Acta Chem. Scand. B 29, 715 [1975]).

In the present case of anodic oxidation by means of intermediate trifluoroacetoxylation, one would have expected (even in the light of the survey by Kunihisa Yoshida, Electrooxidation in Organic Chemistry, The Role of Cation Radicals as Synthetic Intermediates, A Wiley-Interscience Publication, John Wiley and Sons, New York, particularly page 209) that in addition to the 4-hydroxy-1,2-benzisothiazol-2(3H)-one-1,1-dioxide the isomers with hydroxy groups in the other positions on the aromatic group would occur, resulting in a reduction of the yield of the compound of formula I and leading to serious difficulties in isolating the pure compound. However, instead, when the compound of formula II is subjected to anodic oxidation, only the compound of formula I is formed, and by a judicious choice of measures this conversion can be carried out virtually quantitatively. In the light of the prior art this selectivity of oxidation is surprising.

We should not fail to mention that the compound of formula II has been used for decades in galvanising, particularly as an additive to nickel baths. However, nobody has hitherto observed and described the fact that this compound is oxidatively hydroxylated in the process (I. Dubsky and P. Kozak, Metalloberfläche Angewandte Elektrochemie 27, page 217 to 227, 1973, particularly page 223, column 1). To summarise, it can be stated that the oxidation of compound II exclusively to compound I was not foreseeable.

The following Examples are intended to illustrate the essence of the invention:

EXAMPLE 1

4.6 g (25 mmol) of 1,2-benzisothiazol-3(2H)-one-1,1-dioxide (Saccharin ®) were dissolved in a mixture of 65 ml of methylene chloride, 35 ml of trifluoroacetic acid and 2.1 g of tetraethylammonium tetrafluoroborate. The solution was electrolysed at ambient temperature in an electrolysis trough without any separation of the cathode and anode spaces (undivided cell) using a platinum coil (diameter of wire 1 mm, diameter of coil 0.5 cm, length of coil 7.5 cm) as cathode and a cylindrical platinum wire gauze (cylinder diameter 3.5 cm, cylinder height 5 cm, cylinder surface area 5 $cm^2$) as anode. A dry rectifier with potentiometer was used as the source of current. An ammeter connected in series was used to determine the ampere hours and a voltage meter served to measure the potential between the cathode and anode (about 5 to 7 volts). After a charge quantity of about 0.5 Ah had been used up, electrolysis was stopped. The solution was added to ice water. The organic phase was separated off and combined with the chloroform extracts of the aqueous phase. After evaporation of the solvent the residue was distributed between an aqueous iron (III) chloride solution and methylene chloride. 2.7 g of starting material were recovered from the methylene chloride phase. The iron (III) chloride solution was made alkaline and filtered. The filtrate was then acidified and extracted with methylene chloride. After evaporation and recrystallisation from water, 1.2 g of 4-hydroxy-1,2-benzisothiazol-3(2H)-one-1,1-dioxide were obtained. This corresponds to a yield of 58% based on the starting material reacted and a current yield of 67%.

Melting point: 228° C.

MS: 199 (M+), 136, 119 and 108 m/e $C_7H_5NO_4S$ (199.19): Calculated: C 42.20, H 2.53, N 7.03, S 16.10. Found: C 42.25, H 2.62, N 7.02, S 16.00.

The presence of an isomeric 5- or 6- or 7-hydroxy compound could not be detected.

EXAMPLE 2

The reaction was carried out using the method described in Example 1. Unreacted starting material was removed by column chromatography on silica gel (MN silica gel 60; 0.063 to 0.2 mm; Macherey+Nagel, 5160 Düren, Art.-No. 81533) using ethylene chloride/ethyl acetate/glacial acetic acid (100:30:5) as eluant.

First, 2.65 g of the unreacted starting product were eluted, then, after subsequent crystallisation, the end product was obtained in a 61% yield (based on material reacted);

Melting point: 228° C.

$C_7H_5NO_4S$ (199.19): Calculated: C 42.40, H 2.53, N 7.03, S 16.10. Found: C 42.30, H 2.64, N 7.05, S 16.10.

EXAMPLE 3

4.6 g (25 mmol) of 1,2-benzisothiazol-3(2H)-one-1,1-dioxide (Saccharin ®) were dissolved in a mixture of 65 ml of methylene chloride, 35 ml of trifluoroacetic acid and 2.1 g of tetraethylammonium-tetrafluoroborate. This solution was electrolysed at ambient temperature in an electrolysis vessel with a diaphragm (glass frit) using a round platinum wire gauze (diameter of cathode 5 cm, diameter of anode 6 cm, gap between the electrode surfaces 2 cm) in the cathode and anode spaces. Working up was as in Example 1. The yield of 4-hydroxy-1,2-benzisothiazol-3(2H)-one-1,1-dioxide was 56% (based on material reacted);

Melting point: 228° C.

$C_7H_5NO_4S$ (199.19); Calculated: C 42.20, H 2.53, N 7.02, S 16.10. Found: C 42.14, H 2.70, N 6.95, S 16.00.

EXAMPLE 4

The reaction was analogous to that described in Example 1, but 0.2 mol of trifluoroacetic anhydride was used for each mol of starting compound. Yield of 4-hydroxy-1,2-benzisothiazol-3(2H)-one-1,1-dioxide: 62% (based on starting material reacted).

EXAMPLE 5

The method was analogous to that described in Example 1, but 50 ml of trifluoroacetic acid and 50 ml of methylene chloride were used as solvent and 6.8 g (0.5 molar) of sodium trifluoroacetate were used as conducting salt. Yield: 56% (based on starting material reacted).

EXAMPLE 6

The method was analogous to that described in Example 5 but 0.5 g of trifluoroacetic anhydride was additionally used. Yield: 58% (based on starting material reacted).

EXAMPLE 7

The method was analogous to that of Example 3, but sodium trifluoroacetate (0.5 molar) was used as conducting salt and trifluoroacetic acid and methylene chloride were used in a ratio by volume of 1:1. Yield: 52% (based on starting material reacted).

EXAMPLE 8

The method was analogous to that of Example 7, except that 1 g of trifluoroacetic anhydride was additionally used. Yield: 56% (based on starting material reacted).

EXAMPLE 9

The method was analogous to that described in Example 1 except that 0.5 mol of sodium trifluoroacetate was used per mol of the starting compound. Yield: 59% (based on starting material reacted).

EXAMPLE 10

The method was as described in Example 1 but without methylene chloride as solvent. Instead, 50 ml of trifluoroacetic acid were used. Yield: 52% (based on starting material reacted).

EXAMPLE 11

The method was as described in Example 10; in addition, a further 20 ml of trifluoroacetic anhydride and 5 g of sodium trifluoroacetate were added. Yield: 65% (based on starting material reacted).

EXAMPLE 12

The method was as described in Example 1 except that 2.5 g of tetrabutylammonium tetrafluoroborate were used instead of tetraethylammonium tetrafluoroborate Yield: 56% of theory. If the equivalent quantity of tetrabutylammonium perchlorate was used instead, a yield of 52% was achieved (based on starting material reacted).

EXAMPLE 13

The method was as described in Example 1; instead of 65 ml of methylene chloride, a mixture of 35 ml of methylene chloride and 35 ml of trifluoromethane sulfonic acid was used (v:v=1:1).

EXAMPLE 14

4.6 g (25 mmol) of 1,2-benzisothiazol-3(2H)-one-1,1-dioxide (Saccharin ®) were dissolved in 30 ml of trifluoroacetic acid and mixed with 4 g of sodium trifluoroacetate. The solution was electrolysed analogously to Example 1. After a charge quantity of 0.4 Ah had been used up the solution was added to water. It was extracted with chloroform and worked up as in Example 1. In addition to 3.3 g of starting material, 0.92 g of 4-hydroxy-1,2-benzisothiazol-3(2H)-one-1,1-dioxide were obtained after recrystallisation from water. This corresponds to a yield of 61% based on the starting material reacted;

Melting point: 228° C.

MS: 199 (M+), 136, 119 and 108 m/e.

$C_7H_5NO_4S$ (199.19): Calculated: C 42.20, H 2.53, N 7.03, S 16.10. Found: C 41.98, H 2.48, N 7.06, S 16.20.

Once again a search for isomers in the finished reaction mixture was fruitless.

We claim:

1. Process for preparing 4-hydroxy-1,2-benzisothiazol-3(2H)-one-1,1-dioxide which comprises the steps of anodically oxidizing 1,2-benzoisothiazol-3(2H)-one-1,1-dioxide in the presence of trifluoroacetic acid or trifluoromethanesulfonic acid and a conducting salt in order to yield an intermediate of the formula

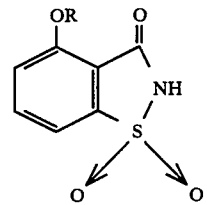

wherein R is $CF_3CO-$ or $CF_3SO_2-$, and then hydrolyzing the resulting intermediate to yield the product.

2. The process of claim 1 wherein the anodic oxidation is carried out in an organic solvent.

3. The process of claim 2, characterised in that the solvent used is dichloromethane, sulfolane, acetonitrile, dimethylformamide, dimethylsulfoxide, dimethylacetamide, tetrahydrofuran, pyridine, acetic acid or nitromethane or mixtures of these substances and the conducting salt used is a tetraalkylammonium tetrafluoroborate, alkali metal trifluoroacetate or alkali metal perchlorate.

4. The process of claim 3, characterised in that aluminium oxide or trifluoro-acetic anhydride is also present in the reaction mixture.

5. The process of claim 1, characterised in that a charge quantity of from 2 to 4 F per mol of reacted educt is used.

6. The process of claim 1, characterised in that oxide electrodes or electrodes of noble metals or lead electrodes, glassy carbon electrodes or carbon electrodes are used.

7. The process of claim 1, characterised in that the anode space is protected from the cathode space by a diaphragm.

8. A process for preparing a compound of the formula

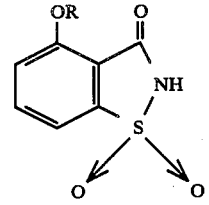

wherein R is $CF_3CO-$ or $CF_3SO_2-$ which comprises anodically oxidizing 4-hydroxy-1,2-benzisothiazol-3(2H)-one-1,1-dioxide in the presence of trifluoroacetic acid or trifluorosulfonic acid and a conducting salt.

* * * * *